United States Patent
Yamazaki et al.

(10) Patent No.: US 8,669,390 B2
(45) Date of Patent: Mar. 11, 2014

(54) PROCESS FOR PRODUCTION OF CYCLIC SILANE COMPOUND AND/OR CYCLIC CARBOSILANE COMPOUND

(75) Inventors: Satoru Yamazaki, Niigata-ken (JP); Kimihiko Oohata, Chiba-ken (JP); Minoru Okada, Niigata-ken (JP); Masamichi Yasuhara, Niigata-ken (JP)

(73) Assignee: Nippon Soda Co., Ltd., Tokyo (JP)

( * ) Notice: Subject to any disclaimer, the term of this patent is extended or adjusted under 35 U.S.C. 154(b) by 268 days.

(21) Appl. No.: 13/259,554

(22) PCT Filed: Apr. 9, 2010

(86) PCT No.: PCT/JP2010/056473
§ 371 (c)(1),
(2), (4) Date: Sep. 23, 2011

(87) PCT Pub. No.: WO2010/119825
PCT Pub. Date: Oct. 21, 2010

(65) Prior Publication Data
US 2012/0016149 A1  Jan. 19, 2012

(30) Foreign Application Priority Data

Apr. 13, 2009  (JP) ................. 2009-096720
Apr. 13, 2009  (JP) ................. 2009-096721

(51) Int. Cl.
*C07F 7/21*  (2006.01)

(52) U.S. Cl.
USPC ........................................ 556/430; 556/400

(58) Field of Classification Search
USPC .......................... 556/406, 400, 430
See application file for complete search history.

(56) References Cited

U.S. PATENT DOCUMENTS

| | | | | |
|---|---|---|---|---|
| 5,252,766 A | * | 10/1993 | Sakakura et al. | ............. 556/430 |
| 5,700,400 A | * | 12/1997 | Ikai et al. | ...................... 252/513 |
| 2012/0263639 A1 | * | 10/2012 | Brausch et al. | ............... 423/347 |

FOREIGN PATENT DOCUMENTS

| JP | A-54-24874 | 2/1979 |
|---|---|---|
| JP | A-54-130541 | 10/1979 |
| JP | A-60-178893 | 9/1985 |
| JP | A-61-238790 | 10/1986 |
| JP | A-7-252270 | 10/1995 |

OTHER PUBLICATIONS

Kumada, M. et al., "Silicon-Containing Heterocyclic Compounds I. Preparation and Reactions of 1,1,2,2-Tetramethyl-1,2-Disilacycloalkanes, From Disilacyclopentane to Disilacyclooctane," *Journal of Organometallic Chemistry*, 1967, pp. 43-55, vol. 9.
International Search Report issued in International Application No. PCT/JP2010/056473 on Jul. 20, 2010 (with translation).
Song et al., "A Study on the Pyrolysis of Polydimethylsilane," ACTA Polymerica Sinica, vol. 6, pp. 753-757, Dec. 1995 with English-language translation.
Fritz et al., "Über die Bildung Cyclischer Carbosilane durch Umsetzung mit AlBr₃," Z. Anorg. Allg. Chem., vol. 497, pp. 21-55, 1983 with partial English-language translation.
Sep. 3, 2013 Notification of First Office Action issued in Chinese Application No. 201080016055.1 with English-language translation.

* cited by examiner

*Primary Examiner* — Johann R Richter
*Assistant Examiner* — Pancham Bakshi
(74) *Attorney, Agent, or Firm* — Oliff PLC

(57) ABSTRACT

The present invention relates to: a process for producing a cyclic silane compound, which comprises subjecting a chained polysilane to pyrolysis in the presence of an oxide of a transition metal belonging to Group 8 or Group 11 of the periodic table; and a process for producing a cyclic carbosilane compound, which comprises subjecting a chained polysilane to pyrolysis in the presence of a simple substance of a metal selected from the group consisting of transition metal elements and elements belonging to Groups 12 to 15 of the periodic table or a compound thereof.

5 Claims, No Drawings

PROCESS FOR PRODUCTION OF CYCLIC SILANE COMPOUND AND/OR CYCLIC CARBOSILANE COMPOUND

TECHNICAL FIELD

The present invention relates to a process for producing a cyclic silane compound and/or a cyclic carbosilane compound. More specifically, it relates to a process for providing a cyclic silane compound or a cyclic carbosilane compound from a chained polysilane with good selectivity and safety by using a specific metal simple substance or metal compound.

BACKGROUND ART

In the field of production intermediates of organosilicon chemistry, a cyclic silane compound is one of the important starting materials.

Heretofore, for example, decamethylcyclopentasilane is obtained as a by-product in the production of chained polysilanes or cyclohexasilanes by a dechlorination reaction of dimethyldichlorosilane using an alkali metal or alkali earth metal, so that both yield and purity are low.

As an alternative process, there is known a process for synthesizing decamethylcyclopentasilane by pyrolyzing a chained polysilane under an inert gas atmosphere but both yield and purity are also low by this process.

As a process which dissolves these disadvantages, Patent Document 1 describes a process for producing decamethylcyclopentasilane where poly(dimethylsilylene) is continuously transferred into and passed through a heated vacant tube under an inert gas atmosphere to effect pyrolysis.

However, the process also has a problem that a strict control of reaction time is required since decamethylcyclopentasilane formed may be pyrolized when the reaction time is prolonged.

Moreover, heretofore, a cyclic carbosilane compound which is important as a production intermediate for organosilicon polymers, especially, a precursor for chained polycarbosilanes, has been mainly produced by ring closure through a dechlorination reaction of terminal chlorosilyl groups of a halosilane compound using an alkali metal or an alkali earth metal, as shown in the following scheme (Non-Patent Document 1).

[Chem 1]

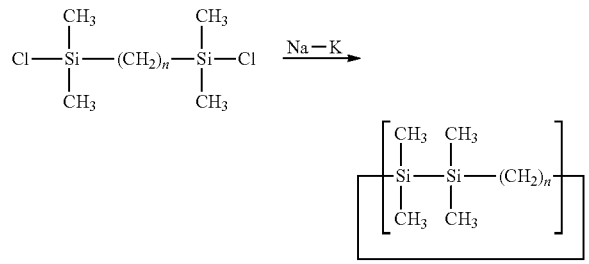

However, this process has a problem that the number of carbon atoms is larger than the number of silicon atoms and hence the process only synthesizes those having low silicon content.

On the other hand, it is also known that a cyclic carbosilane is produced by metathesis of a silicon-silicon bond of a cyclic disilane having a low molecular weight using a palladium catalyst (Patent Document 2). However, the process is limited to the production of a macrocyclic carbosilane.

BACK GROUND ART DOCUMENTS

Patent Documents

Patent Document 1; JP-A-61-238790
Patent Document 2: JP-A-07-252270

Non-Patent Document

Non-Patent Document 1: J. Organometal. Chem. (1967), 9, 43

SUMMARY OF THE INVENTION

Problems that the Invention is to Solve

An object of the present invention is to provide a process for producing a cyclic silane compound (especially, cyclopentasilane or the like) or a cyclic carbosilane compound (especially, 6- to 8-membered cyclic carbosilane compounds) steadily and safely with good selectivity.

Means for Solving the Problems

As a result of the extensive studies, the present inventors have found that, in the process for producing a cyclic silane compound and/or a cyclic carbosilane by pyrolyzing a chained polysilane, the objective compounds are efficiently obtained and formation selectivity between the cyclic silane compound and the cyclic carbosilane compound to be obtained can be controlled by carrying out the reaction in the presence of a specific metal simple substance or metal compound. Specifically, they have found that the cyclic silane compound is efficiently obtained in the presence of an oxide of a transition metal belonging to Group 8 or Group 11 of the periodic table, especially an iron compound or a copper compound. Also, they have found that a cyclic carbosilane compound mainly containing 6- to 8-membered cyclic carbosilanes is efficiently obtained in the presence of a metal simple substance or a metal compound of a transition metal element or an element belonging to Groups 12 to 15 of the periodic table. Based on these findings, the invention is accomplished.

That is, the first embodiment of the present invention relates to the following process for producing a cyclic silane compound:

[1] a process for producing a cyclic silane compound, which contains subjecting a chained polysilane to pyrolysis in the presence of an oxide of a transition metal belonging to Group 8 or Group 11 of the periodic table;

[2] the process for producing a cyclic silane compound according to the above [1], in which the chained polysilane is a compound represented by the following formula (1):

[Chem 2]

(1)

in the formula, $R^1$ and $R^2$ each independently represent a C1-C6 alkyl group, an aryl group, or an arylalkyl group; X represents a hydrogen atom, a halogen atom, a hydroxyl group, a C1-C6 alkyl group, a C1-C6 alkoxy group, an aryl group, or a trialkylsiloxy group; m represents any integer of 2 to 50,000; and each of $R^1$ groups and $R^2$ groups may be the same or different from each other;

[3] the process for producing a cyclic silane compound according to the above [1] or [2], in which the cyclic silane compound is a compound represented by the following formula (2):

[Chem 3]

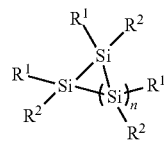
(2)

in the formula, $R^1$ and $R^2$ represent the same meanings as in the formula (1); n represents any integer of 1 to 20; $R^1$ and $R^2$ may be the same or different from each other; and each of $R^1$ groups and $R^2$ groups may be the same or different from each other;

[4] the process for producing a cyclic silane compound according to any one of the above [1] to [3], in which the cyclic silane compound is decamethylcyclopentasilane; and

[5] the process for producing a cyclic silane compound according to any one of the above [1] to [4], in which the transition metal belonging to Group 8 of the periodic table is iron and the transition metal belonging to Group 11 of the periodic table is copper.

Further, the second embodiment of the present invention relates to the following process for producing a cyclic carbosilane compound:

[6] a process for producing a cyclic carbosilane compound, which comprises subjecting a chained polysilane to pyrolysis in the presence of a simple substance of a metal selected from the group consisting of transition metal elements and elements belonging to Groups 12 to 15 of the periodic table or a compound thereof;

[7] the process for producing a cyclic carbosilane compound according to the above [6], in which the chained polysilane is a compound represented by the formula (1);

[8] the process for producing a cyclic carbosilane compound according to the above [6] or [7], in which the cyclic carbosilane compound is 6- to 8-membered cyclic carbosilane compounds; and

[9] the process for producing a cyclic carbosilane compound according to any one of the above [6] to [8], in which the transition metal element is titanium, manganese, iron, cobalt, or palladium, and the element belonging to Groups 12 to 15 of the periodic table is aluminum, silicon, zinc, cadmium, tin, antimony, lead, or bismuth.

Advantage of the Invention

According to the production process of the first embodiment of the present invention, a cyclic silane compound, especially decamethylcyclopentasilane can be efficiently obtained. Moreover, according to the production process of the second embodiment of the present invention, a cyclic carbosilane compound, especially 6- to 8-membered cyclic carbosilane compounds can be efficiently obtained.

MODE FOR CARRYING OUT THE INVENTION

The present invention is an invention according to a production process, which affords a cyclic silane compound and/or a cyclic carbosilane compound using a chained polysilane as a raw material. The chained polysilane herein is a chained polymer having a —Si—Si— bond as a skeleton thereof. For example, a silane compound represented by the general formula (1) can be exemplified.

[Chem 4]

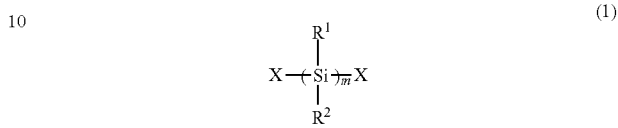
(1)

In the formula, $R^1$ and $R^2$ each independently represent a C1-C6 alkyl group, an aryl group, or an arylalkyl group; X represents a hydrogen atom, a halogen atom, a hydroxyl group, a C1-C6 alkyl group, a C1-C6 alkoxy group, an aryl group, or a trialkylsiloxy group; m represents any integer of 2 to 50,000; and each of $R^1$ groups and $R^2$ groups may be the same or different from each other.

As the C1-C6 alkyl group for $R^1$ and $R^2$, i.e., a chained or branched alkyl group having 1 to 6 carbon atoms, for example, there may be mentioned a methyl group, an ethyl group, a n-propyl group, an isopropyl group, a n-butyl group, an isobutyl group, a t-butyl group, a n-pentyl group, an isopentyl group, a neopentyl group, a 2-methylbutyl group, a 2,2-dimethylpropyl group, a n-hexyl group, and the like.

The aryl group means a monocyclic or polycyclic aryl group and, in the case of the polycyclic aryl group, includes partially saturated groups in addition to fully unsaturated groups. For example, there may be mentioned a phenyl group, a naphthyl group, an azulenyl group, an indenyl group, an indanyl group, a tetralinyl group, and the like. Of these, preferred are C6-C10 aryl groups.

As the aralkyl group, there may be mentioned a benzyl group, a phenethyl group, a 3-phenyl-n-propyl group, a 1-phenyl-n-hexyl group, a naphthalen-1-ylmethyl group, a naphthalen-2-ylethyl group, a 1-naphthalen-2-yl-n-propyl group, an inden-1-ylmethyl group, and the like. Preferred are C6-C10 aryl-C1-C6 alkyl groups.

As the halogen atom for X, fluorine, chlorine, bromine, iodine, and the like may be mentioned. As the C1-C6 alkyl group for X, those the same as the C1-C6 alkyl groups for $R^1$ may be mentioned. As the C1-C6 alkoxy group, specifically, there may be mentioned a methoxy group, an ethoxy group, a n-propoxy group, an isopropoxy group, a n-butoxy group, an isobutoxy group, a s-butoxy group, a t-butoxy group, a n-pentoxy group, an isopentoxy group, a neopentoxy group, a 4-methylbutoxy group, a 1-ethylpropoxy group, a n-hexyloxy group, an isohexyloxy group, a 4-methylpentoxy group, a 3-methylpentoxy group, a 2-methylpentoxy group, a 1-methylpentoxy group, a 3,3-dimethylbutoxy group, a 2,2-dimethylbutoxy group, a 1,1-dimethylbutoxy group, a 1,2-dimethylbutoxy group, a 1,3-dimethylbutoxy group, a 2,3-dimethylbutoxy group, a 1-ethylbutoxy group, a 2-ethylbutoxy group, and the like.

As the trialkylsiloxy group, a trimethylsiloxy group, a triethylsiloxy group, a t-butyldimethylsiloxy group, and the like can be mentioned. The trialkylsiloxy group has three alkyl groups in one substituent and these three alkyl groups may be the same or different from each other. The alkyl group is preferably a C1-C6 alkyl group. Specifically, those the same as the alkyl groups for $R^1$ may be mentioned.

The m represents any integer of 2 to 50,000.

As the cyclic silane compound obtained by the production process of the present invention, a compound represented by the formula (2) and the like can be exemplified.

[Chem 5]

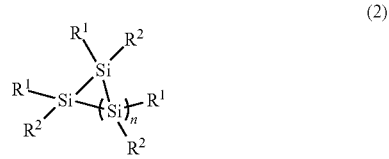

(2)

In the formula, $R^1$ and $R^2$ represent the same meanings as in the formula (1); n represents any integer of 1 to 20; $R^1$ and $R^2$ may be the same or different from each other; and each of $R^1$ groups and $R^2$ groups may be the same or different from each other.

As $R^1$ and $R^2$, groups the same as those mentioned for the formula (1) can be exemplified, and the n represents any integer of 1 to 20 and is more preferably any integer of 3 to 8. Namely, the cyclic silane compound of the present invention is preferably a compound having a cyclopentasilane ring, a cyclohexasilane ring, a cycloheptasilane ring, or a cyclooctasilane ring.

As the cyclic silane compound, specifically peralkylcyclosilanes, more specifically, for example, decamethylcyclopentasilane, dodecamethylcyclohexasilane, and the like may be mentioned.

According to the production process of the first embodiment of the present invention, in the production of a cyclic silane, the process is carried out in the presence of an oxide of a transition metal belonging to Group 8 or Group 11 of the periodic table. The objective cyclic silane can be obtained with good selectivity by carrying out the reaction in the presence of the metal oxide. Moreover, the formation selectivity between the cyclic silane compound and the cyclic carbosilane compound to be obtained can be controlled depending on the amount of the metal oxide to be added.

The cyclic carbosilane compound herein is a cyclic compound having a skeleton composed of silicon and carbon and partially having a silicon-carbon-silicon bond.

As the transition metal belonging to Group 8 of the periodic table, iron, ruthenium, and osmium may be mentioned. As the transition metal belonging to Group 11, copper, silver, and gold may be mentioned. As oxides of these transition metals, iron (II) oxide, iron (II, III) oxide, iron (III) oxide, ruthenium dioxide, ruthenium tetroxide, osmium dioxide, osmium tetroxide, copper (I) oxide, copper (II) oxide, silver oxide, and the like may be mentioned. Of these, more preferably, the transition metal belonging to Group 8 is iron and the transition metal belonging to Group 11 is copper. Above all, they are more preferably iron oxide (III) and copper (II) oxide.

In the production process of the first embodiment of the present invention, these metal oxides may be used singly, or two or more thereof may be used in combination.

In the production process of the first embodiment of the present invention, the amount of the metal oxide to be used is preferably 10 ppm by weight or more, more preferably 100 ppm by weight or more, and further preferably 1,000 ppm by weight or more based on the chained polysilane to be used. Moreover, it is preferred to be 2,000 ppm by weight or less.

Incidentally, any components other than the above metal oxides may be added unless the components inhibit the production process of the first embodiment of the present invention.

The production of the cyclic silane compound in the production process of the first embodiment of the present invention is carried out by charging a chained polysilane as a raw material and the above metal oxide into a reaction vessel and heating them. By heating, the chained polysilane is pyrolyzed to form the cyclic silane compound.

The reaction temperature may be appropriately selected depending on the amount to be charged and the apparatus but is approximately 350 to 450° C., and preferably about 400° C. The reaction time may be appropriately selected depending on the amount to be charged, the temperature, and the apparatus but is approximately 10 minutes to 90 minutes.

Moreover, the reaction is preferably carried out under normal pressure and an inert gas stream, and as the inert gas, nitrogen, argon, mixed gases thereof, and the like may be mentioned.

The cyclic silane compound produced by the above process can be confirmed by known methods such as gas chromatography (GPC) and infrared spectroscopic (IR) analysis.

The cyclic carbosilane compound obtained by the production process of the second embodiment of the present invention is a cyclic compound having a skeleton composed of silicon and carbon and partially having a bond of silicon-carbon-silicon, and especially, 6- to 8-membered cyclic carbosilane compounds are efficiently obtained.

As the 6- to 8-membered cyclic carbosilane compounds, for example, in the case where poly(dimethylsilylene) is used as a raw material, compounds represented by the following formulae (3) to (5) and the like can be exemplified. However, these chemical structures are presumed based on the results of gas chromatography-mass spectroscopy (GC-MS) and infrared spectroscopic (IR) analysis (absorption derived from Si—H stretching vibration $v_{Si-H}$).

[Chem 6]

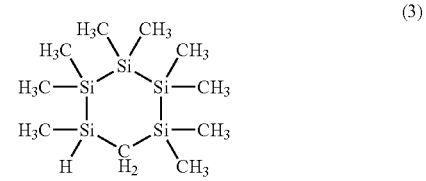

(3)

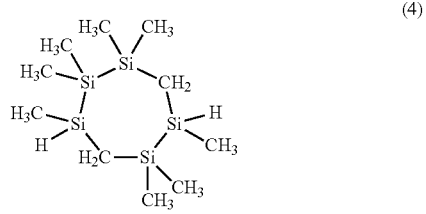

(4)

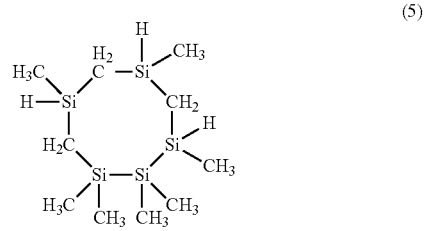

(5)

Moreover, in the invention, cyclic silanes represented by the following formula, decomposition products of the chained polysilane, and the like are also produced as by-products.

[Chem 7]

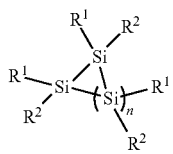

In the formula, $R^1$ and $R^2$ represent the same meanings as in the formula (1); n represents any integer of 1 to 20; $R^1$ and $R^2$ may be the same or different from each other; and each of $R^1$ groups and $R^2$ groups may be the same or different from each other.

As $R^1$ and $R^2$, groups the same as those mentioned for the formula (1) can be exemplified and the n is any integer of 1 to 20. Specifically, peralkylcyclosilanes, more specifically, for example, decamethylcyclopentasilane, dodecamethylcyclohexasilane, and the like may be mentioned.

The process for producing a cyclic carbosilane compound of the present invention is carried out in the presence of a metal simple substance selected from the group consisting of transition metal elements and elements belonging to Groups 12 to 15 of the periodic table or a compound thereof (hereinafter referred to as a "metal additive" when they are collectively described). By carrying out the reaction in the presence of the metal additive, a cyclic carbosilane compound, particularly 6- to 8-membered carbosilane compounds can be efficiently obtained.

As the transition metal, titanium (Ti), manganese (Mn), iron (Fe), cobalt (Co), palladium (Pd), or the like may be mentioned.

There may be mentioned zinc (Zn), cadmium (Cd), and the like as the elements belonging to Group 12 of the periodic table, aluminum (Al) and the like as the elements belonging to Group 13, silicon (Si), tin (Sn), lead (Pb), and the like as the elements belonging to Group 14, and antimony (Sb), bismuth (Bi), and the like as the elements belonging to Group 15.

As the metal simple substance, specifically, Zn and the like may be mentioned.

Moreover, as the metal compound, there may be mentioned $TiCl_4$, $MnCl_2$, $FeCl_2$, $CoCl_2$, $PdCl_2$, $ZnCl_2$, $ZnO$, $CdCl_2$, $AlCl_3$, $SiCl_4$, $SnCl_2$, $SnCl_4$, $SnO$, $SnO_2$, $PbCl_2$, $SbCl_5$, $BiCl_3$, and the like. Of these, $ZnCl_2$, $ZnO$, $AlCl_3$, $SnCl_2$, $SnCl_4$, $PbCl_2$, $SbCl_5$, and $BiCl_3$ are particularly preferred. In this connection, the metal compound is preferably not an oxide of a transition metal belonging to Group 8 or Group 11.

In the production process of the second embodiment of the present invention, these metal additives may be used alone or in combination of two or more thereof.

In the production process of the second embodiment of the present invention, the amount of the metal additive to be used is preferably 1 to 2,000 ppm by weight, and more preferably 1 to 100 ppm by weight based on the chained polysilane to be used.

Incidentally, any components other than the above metal additives may be added unless the components inhibit the production process of the second embodiment of the present invention.

The production of the cyclic carbosilane compound of the present invention is carried out by charging a chained polysilane as a raw material and the above metal additive into a reaction vessel and heating them. By heating, the chained polysilane is pyrolyzed to form the cyclic carbosilane compound.

The reaction temperature may be appropriately selected depending on the amount to be charged and the apparatus but is usually 350 to 450° C., and preferably about 400° C., The reaction time may be appropriately selected depending on the amount to be charged, the temperature, and the apparatus but is usually 10 minutes to 90 minutes.

Moreover, the reaction is preferably carried out under normal pressure and an inert gas stream, and as the inert gas, nitrogen, argon, and mixed gases thereof may be mentioned.

The cyclic carbosilane compound produced by the above process can be confirmed by known methods such as gas chromatography (GPC) and infrared spectroscopic (IR) analysis.

EXAMPLES

The following will describe the production process of the first embodiment of the present invention but the first embodiment of the present invention is not restricted to these Examples.

Example 1

Into a reaction vessel were charged 20.40 g of poly(dimethylsilylene) (trade name: PDMS, manufactured by Nippon Soda Co., Ltd.) and 0.2 mg (10 ppm by weight based on PDMS) of iron (III) oxide (manufactured by Wake Pure Chemical Industries, Ltd.), and pyrolysis (elevating the temperature from room temperature to about 400° C. over a period of 40 minutes and subsequent heating at about 400° C. for 50 minutes) was carried out under a nitrogen stream.

Examples 2 to 8, Comparative Example 1

Pyrolysis of poly(dimethylsilylene) was carried out as described in Table 1 in the same manner as in Example 1 except that the kind and amount of the metal oxide used were changed. In this regard, (ppm) in the table represents (ppm by weight).

TABLE 1

| | Metal oxide | Manufacturer | Amount charged(ppm) |
| --- | --- | --- | --- |
| Example 2 | Iron (III) oxide | Wako Pure Chemical Industries, Ltd. | 100 |
| Example 3 | Iron (III) oxide | Wako Pure Chemical Industries, Ltd. | 1000 |
| Example 4 | Silver oxide | Wako Pure Chemical Industries, Ltd. | 1000 |
| Example 5 | Copper (I) oxide | Kanto Chemical Co., Inc. | 1000 |
| Example 6 | Copper (II) oxide | Wako Pure Chemical Industries, Ltd. | 10 |
| Example 7 | Copper (II) oxide | Wako Pure Chemical Industries, Ltd. | 100 |
| Example 8 | Copper (II) oxide | Wako Pure Chemical Industries, Ltd. | 1000 |
| Comparative Example 1 | none | | none |

(Analysis of Product)

Reaction products obtained in Examples 1 to 8 were analyzed by gas chromatography (GC).
Measurement conditions are as follows.
GC apparatus: GC-14A (manufactured by Shimadzu Corporation)
Column: Glass column 7G 3.2 mmϕ×2.1 m (manufactured by Shimadzu Corporation)

Filler: Silicone OV-17 2% Chromosorb WAW DMCS 60/80 mesh (manufactured by G L Sciences Inc.)
Injection temperature: 200° C.
Column temperature: 100° C. (10 minutes)-20° C./minute-250° C. (5 minutes)
Detector: TCD 125 mA, 220° C.
Carrier gas: helium 100 mL/minute
Injection amount: 0.6 μL
Data processing apparatus: Chromatopack C-R6A (manufactured by Shimadzu Corporation)
(Evaluation of Product)

For pyrolysis products obtained in Examples 1 to 8 and Comparative Example 1, the ratio (A/B) of the area of the peak (A) (retention time 4.8 minutes) containing a cyclic carbosilane compound on GC to the area of the peak (B) (retention time: 4.0 minutes) of decamethylcyclopentasilane on GC and the area value of B are shown in Table 2. Prom these results, it was revealed that the A/B value decreased in Examples where a metal oxide was added as compared with Comparative Example 1 where pyrolysis of poly(dimethylsilylene) was carried out without adding any substances, and the amount of the cyclic silane compound formed could be relatively increased as compared to the cyclic carbosilane compound by adding a metal oxide. Moreover, it was revealed that the area value indicating the amount of formed decamethylcyclopentasilane increased in Examples where a metal oxide was added as compared to Comparative Example 1 (particularly, in the case where an oxide of copper or iron was used), and the amount thereof formed could be increased by adding a metal oxide.

TABLE 2

|  | A/B value | B area value |
| --- | --- | --- |
| Example 1 | 1.19 | 26,754 |
| Example 2 | 1.07 | 26,958 |
| Example 3 | 0.79 | 34,430 |
| Example 4 | 1.24 | 23,473 |
| Example 5 | 0.29 | 78,973 |
| Example 6 | 0.79 | 34,780 |
| Example 7 | 0.40 | 61,613 |
| Example 8 | 0.21 | 95,087 |
| Comparative Example 1 | 1.30 | 22,389 |

The following will describe the production process of the second embodiment of the present invention but the second embodiment of the present invention is not restricted to these Examples.

Example 9

Into a reaction vessel were charged 20.6 g of poly(dimethylsilylene) (trade name: PDMS, manufactured by Nippon Soda Co., Ltd.) and 24 mg (1,170 ppm by weight based on PDMS) of $AlCl_3$ (manufactured by Wake Pure Chemical Industries, Ltd.), and pyrolysis (elevating the temperature from room temperature to 400° C. over a period of 45 minutes and subsequent heating at about 400° C. for 30 minutes) was carried out under a nitrogen stream.

Examples 10 to 24, Comparative Example 2

Pyrolysis of poly(dimethylsilylene) was carried out as described hi Table 3 in the same manner as in Example 9 except that the kind and amount of the metal additive used were changed.

TABLE 3

|  | Chloride or oxide | Amount added (ppm by weight) |
| --- | --- | --- |
| Example 10 | $ZnCl_2$ | 100 |
| Example 11 | ZnO | 100 |
| Example 12 | $SnCl_2$ | 74 |
| Example 13 | $SnCl_4$ | 100 |
| Example 14 | $SbCl_5$ | 1000 |
| Example 15 | $BiCl_3$ | 1000 |
| Example 16 | $PbCl_2$ | 1000 |
| Example 17 | $FeCl_2$ | 1000 |
| Example 18 | $CdCl_2$ | 1000 |
| Example 19 | $MnCl_2$ | 1000 |
| Example 20 | $TiCl_4$ | 750 |
| Example 21 | $CoCl_2$ | 1000 |
| Example 22 | $SiCl_4$ | 610 |
| Example 23 | $PdCl_2$ | 1000 |
| Example 24 | $ZnCl_2$ | 3.3 |
| Comparative Example 2 | none | — |

(Analysis of Product)

Reaction products obtained in Examples and Comparative Example were analyzed by gas chromatography (GC). Measurement conditions are as follows.
GC apparatus: GC-14A (manufactured by Shimadzu Corporation)
Column: Glass column 7G 3.2 mmφ×2.1 m (manufactured by Shimadzu Corporation)
Filler: Silicone OV-17 2% Chromosorb WAW DMCS 60/80 mesh (manufactured by G L Sciences Inc.)
Injection temperature: 200° C.
Column temperature: 100° C. (10 minutes)-20° C./minute-250° C. (5 minutes)
Detector: TCD 125 mA, 220° C.
Carrier gas: helium 100 mL/minute
Injection amount: 0.6 μL
Data processing apparatus: Chromatopack C-R6A (manufactured by Shimadzu Corporation)
(Evaluation of Product)

For products of Examples 9 to 24 and Comparative Example 2, the ratio (A/B value) of the area of the peak (A) (retention time: 4.8 minutes) containing the cyclic carbosilane compound of the present invention on GC to the area of the peak (B) (retention time: 4.0 minutes) of decamethylcyclopentasilane on GC and the area value of A are shown in Table 4. From these results, it was revealed that the A/B value increased in Examples where a metal compound was added as compared to Comparative Example 2 where pyrolysis of poly (dimethylsilylene) was carried out without adding any substances, and the amount of the cyclic carbosilane compound formed could be relatively increased as compared to the cyclic silane compound by adding a metal compound. Moreover, it was revealed that the area value indicating the amount of the formed cyclic carbosilane compound increased in Examples (partially with exception) as compared with Comparative Example 2, and the amount thereof formed could be increased by adding the metal compound.

TABLE 4

|  | A/B value | A area value |
| --- | --- | --- |
| Example 9 | 1.14 | 33,505 |
| Example 10 | 1.28 | 25,883 |
| Example 11 | 0.93 | 33,583 |
| Example 12 | 1.48 | 21,259 |
| Example 13 | 1.49 | 21,388 |
| Example 14 | 1.51 | 32,764 |

TABLE 4-continued

|  | A/B value | A area value |
|---|---|---|
| Example 15 | 1.30 | 21,118 |
| Example 16 | 1.24 | 16,188 |
| Example 17 | 0.42 | 16,371 |
| Example 18 | 0.56 | 17,550 |
| Example 19 | 0.40 | 13,754 |
| Example 20 | 0.75 | 33,468 |
| Example 21 | 0.79 | 19,041 |
| Example 22 | 0.44 | 32,183 |
| Example 23 | 0.36 | 15,386 |
| Example 24 | 1.01 | 27,199 |
| Comparative Example 2 | 0.16 | 15,933 |

While the present invention has been described in detail and with reference to the specific embodiments thereof, it will be apparent to one skilled in the art that various changes and modifications can be make therein without departing from the spirit and scope thereof.

The present application is based on Japanese Patent Application No 2009-096720 filed on Apr. 13, 2009 and Japanese Patent Application No 2009-096721 filed on Apr. 13, 2009, and the entire contents thereof are incorporated herein by reference.

The invention claimed is:

1. A process for producing a cyclic silane compound, which comprises subjecting a chained polysilane to pyrolysis in the presence of an oxide of a transition metal belonging to Group 8 or Group 11 of the periodic table.

2. The process for producing a cyclic silane compound according to claim 1, wherein the chained polysilane is a compound represented by the following formula (1):

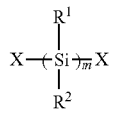
(1)

wherein $R^1$ and $R^2$ each independently represent a C1-C6 alkyl group, an aryl group, or an arylalkyl group; X represents a hydrogen atom, a halogen atom, a hydroxyl group, a C1-C6 alkyl group, a C1-C6 alkoxy group, an aryl group, or a trialkylsiloxy group; m represents any integer of 2 to 50,000; and each of $R^1$ groups and $R^2$ groups may be the same or different from each other.

3. The process for producing a cyclic silane compound according to claim 1, wherein the cyclic silane compound is a compound represented by the following formula (2):

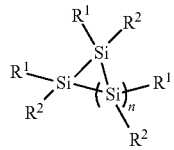
(2)

wherein $R^1$ and $R^2$ represent the same meanings as in formula (1); n represents any integer of 1 to 20; $R^1$ and $R^2$ may be the same or different from each other; and each of $R^1$ groups and $R^2$ groups may be the same or different from each other.

4. The process for producing a cyclic silane compound according to claim 1, wherein the cyclic silane compound is decamethylcyclopentasilane.

5. The process for producing a cyclic silane compound according to claim 1, wherein the transition metal belonging to Group 8 of the periodic table is iron and the transition metal belonging to Group 11 is copper.

* * * * *